United States Patent
Kawasaki

(10) Patent No.: US 9,521,840 B2
(45) Date of Patent: Dec. 20, 2016

(54) FILM-SHAPED TISSUE STORAGE TRANSPORT CONTAINER AND STORAGE TRANSPORT METHOD

(71) Applicant: Terumo Kabushiki Kaisha, Shibuya-ku (JP)

(72) Inventor: Manami Kawasaki, Fujisawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 14/310,357

(22) Filed: Jun. 20, 2014

(65) Prior Publication Data

US 2014/0302602 A1 Oct. 9, 2014

Related U.S. Application Data

(63) Continuation of application No. PCT/JP2012/080567, filed on Nov. 10, 2012.

(30) Foreign Application Priority Data

Dec. 21, 2011 (JP) .................................. 2011-280143

(51) Int. Cl.
*A01N 1/02* (2006.01)
*A61J 1/20* (2006.01)

(52) U.S. Cl.
CPC ............ *A01N 1/0273* (2013.01); *A61J 1/2096* (2013.01)

(58) Field of Classification Search
CPC .............................. A01N 1/0273; A61J 1/2096
USPC ...................................................... 435/307.1
See application file for complete search history.

(56) References Cited

U.S. PATENT DOCUMENTS

| | | | |
|---|---|---|---|
| 5,326,706 A * | 7/1994 | Yland | A01N 1/0247 435/1.2 |
| 2003/0086830 A1 | 5/2003 | Haywood et al. | |
| 2007/0166819 A1 | 7/2007 | Ghosh et al. | |
| 2011/0281352 A1 | 11/2011 | Raeder et al. | |
| 2012/0160714 A1 | 6/2012 | Nozaki | |

FOREIGN PATENT DOCUMENTS

| | | |
|---|---|---|
| JP | 2001-299326 A | 10/2001 |
| JP | 2002-335950 A | 11/2002 |
| JP | 2003-009845 A | 1/2003 |

(Continued)

OTHER PUBLICATIONS

International Search Report (PCT/ISA/210) mailed on Feb. 5, 2013, by the Japanese Patent Office as the International Searching Authority for International Application No. PCT/JP2012/080567.

*Primary Examiner* — Michael Hobbs
(74) *Attorney, Agent, or Firm* — Buchanan Ingersoll & Rooney PC

(57) ABSTRACT

A film-shaped tissue storage transport container and storage transport method. The storage transport container includes: an external container; a coupling mechanism which couples a container main body and a lid member of the external container; an internal container which is positioned within the external container; an interposed unit having elasticity and which is sandwiched between the internal container and the lid member; and a storage fluid with which the internal container is filled. A film-shaped tissue is present in a floating state in the storage fluid with which the internal container is filled.

14 Claims, 10 Drawing Sheets

(56) References Cited

FOREIGN PATENT DOCUMENTS

| | | |
|---|---|---|
| JP | 2003-070460 A | 3/2003 |
| JP | 2005-506526 A | 3/2005 |
| JP | 4213588 B2 | 1/2009 |
| JP | 2009-523417 A | 6/2009 |
| JP | 2010-528983 A | 8/2010 |
| JP | 2012-130311 A | 7/2012 |

* cited by examiner

FILM-SHAPED TISSUE STORAGE TRANSPORT CONTAINER AND STORAGE TRANSPORT METHOD

CROSS REFERENCES TO RELATED APPLICATIONS

This application is a continuation of International Application No. PCT/JP2012/080567 filed on Nov. 27, 2012, and claims priority to Japanese Application No. 2011-280143 filed on Dec. 21, 2011, the entire content of both of which is incorporated herein by reference.

TECHNICAL FIELD

The invention relates to a storage transport container and storage transport method for a film-shaped tissue composed of biological cells (cells derived from a living body).

BACKGROUND ART

In recent years, in therapy of myocardial infarction and the like, there has been widely known a therapeutic method in which a sheet-shaped cell culture obtained by cultivating and organizing the patient's own cells is transplanted to the patient. Such a cell culture may sometimes be generally called a "cell sheet." In order to provide the cultivated cell sheet for transplantation to a patient, the cell sheet needs to be preserved in the state of being contained in a predetermined container filled with a storage fluid such as physiological salt solution and be transported in this state to a medical institution or the like.

For transport of a cell sheet, it may be contemplated to utilize a container assembly as disclosed in Japanese Patent No. 4213588. The container assembly includes a container capable of containing a reagent therein, and a sample holder which is disposed inside the container and is capable of containing a biological sample therein. The sample holder has a fluid opening, through which the reagent can move between the inside and the outside of the sample holder.

The cell sheet is very small in film thickness and is therefore fragile. Thus, when the above-mentioned container assembly is used, the cell sheet is only floating in the storage fluid. When the container assembly is vibrated during transport thereof, the vibration may be transmitted through the storage fluid, resulting in damage to or breakage of the cell sheet. Specifically, when the storage fluid is vibrated due to vibration applied to the container, flowing motion such as waving of the storage fluid is generated, and shearing forces and/or tensile forces are exerted on the cell sheet. Accordingly, a means for preventing the transmission of vibration to the cell sheet is needed.

Japanese Patent Laid-open No. 2002-335950 discloses a storage transport container wherein a film-shaped tissue is held by sandwiching it between liquid-permeable support bodies, and the sandwich-like body is contained in a container together with a predetermined storage fluid so as to keep it in a wet state. When this storage transport container is used for storage and transport of a cell sheet, however, there is a risk of damaging the cell sheet at the time of holding the cell sheet by the support bodies, due to the structure in which the support bodies sandwich the cell sheet therebetween by making direct contact with the cell sheet from both sides.

SUMMARY

The disclosure herein provides a film-shaped tissue storage transport container and storage transport method by which a film-shaped tissue composed of biological (living body-derived) cells can be easily stored and transported, without altering the original shape of the film-shaped tissue and while maintaining the quality and biological activity of the film-shaped tissue.

More particularly, an exemplary embodiment of the disclosure provides a storage transport container for film-shaped tissue, to be used for storage or transport of a film-shaped tissue composed of biological cells, the storage transport container including an external container that includes a container main body having an upper opening portion opening upward, and a lid member configured to close the upper opening portion of the container main body, a coupling mechanism coupling the container main body and the lid member, an internal container which is disposed inside the external container, has a lower opening portion being greater than a plan-view shape of the film-shaped tissue and opening downward, and has a lower end thereof making contact with a bottom section of the container main body to thereby close the lower opening portion, an interposed unit having elasticity and being sandwiched between the internal container and the lid member, and a storage fluid with which the internal container is filled to such an extent that no gas layer is formed within the internal container, wherein the film-shaped tissue is present in a floating state in the storage fluid with which the internal container is filled.

According to the above-mentioned configuration, the film-shaped tissue is present in a floating state in the storage fluid with which the internal container is filled. This ensures that even if the storage transport container is vibrated, the storage fluid inside the internal container is prevented from waving or flowing, so that the film-shaped tissue can be prevented from being damaged or broken. In addition, at the time of taking out the film-shaped tissue, it is unnecessary to transfer the film-shaped tissue and the storage fluid into another container. Therefore, the taking-out operation can be carried out speedily, and the risk of damaging or breaking the film-shaped tissue during a transferring operation can be essentially avoided. Furthermore, even if there are some errors in the shape and/or dimensions of the external container due to production accuracy of the external container, such errors can be absorbed by the elasticity (expandable and contractable property) of the interposed unit. Therefore, the internal container can be fixed within the external container stably and assuredly.

In the storage transport container for film-shaped tissue as described above, preferably, the internal container has a liquid-permeable wall section which faces the bottom section of the container main body with a spacing therebetween and is configured so as to permit passage of liquid therethrough, and the internal container and the interposed unit make secure contact with each other to thereby establish a liquid-tight sealing between the internal container and the interposed unit.

According to the exemplary configuration described above, air can be discharged from the internal container via the liquid-permeable wall section, in an assembly process of the storage transport container; therefore, the internal container can easily be filled with a liquid. In addition, since a liquid-tight sealing is established between the internal container and the interposed unit, flowing-in of air into the internal container via a gap between the internal container and the interposed unit can be prevented.

In the storage transport container for film-shaped tissue, preferably, the internal container has a tube-shaped section opening upward and downward, and the liquid-permeable wall section is provided at an intermediate position in the height direction of the tube-shaped section and is configured in a mesh form.

Further, a large flow path area for passage of a liquid therethrough can be secured at the liquid-permeable wall section. Thus, the liquid-permeable wall section is excellent in liquid-passing property. Therefore, in the assembly process of the storage transport container, the internal container can be swiftly mounted on the bottom section of the container main body.

In the exemplary embodiment of the storage transport container for film-shaped tissue disclosed here, preferably, the interposed unit is disposed above the liquid-permeable wall section in a state of making contact with an inner circumferential surface of the tube-shaped section over the whole circumference in the circumferential direction.

Thus, flowing-in of air into the internal container via a gap between the outer circumferential surface of the interposed unit and the inner circumferential surface of the tube-shaped section can be inhibited and a liquid-tight state inside the internal container is maintained in a suitable manner.

In addition, a further exemplary configuration may be adopted wherein the liquid-permeable wall section is a plate-shaped body provided with a through-hole piercing therethrough in a vertical direction, and the through-hole is closed by the interposed unit.

According to such a configuration, the through-hole is closed by simply disposing the interposed unit between the liquid-permeable wall section and the lid member of the external container. Therefore, a liquid-tight structure can be easily created inside the external container.

Another exemplary configuration may be adopted wherein the internal container includes a liquid-permeable wall section which faces the bottom section of the container main body with a spacing therebetween and is provided with a through-hole piercing therethrough in a vertical direction, and a closing member closing the through-hole is disposed between the liquid-permeable wall section and the interposed unit.

According such a configuration, air can be discharged out of the internal container via the liquid-permeable wall section, so that the internal container can be easily filled with a liquid. Since the through-hole is closed with the closing member after the internal container is filled with a liquid, flowing-in of air into the internal container via the through-hole can be securely prevented. Consequently, the liquid-tight state inside the internal container can be secured in a favorable manner.

In such a storage transport container for film-shaped tissue, preferably, a liquid the same as or different from the storage fluid is present outside the internal container within the external container.

Further, a liquid is present in the surroundings of the internal container, which ensures that flowing-in of air into the internal container via the lower opening portion can be prevented.

The exemplary embodiment of the storage transport container for film-shaped tissue disclosed here, preferably, further includes a stabilization member floating at a liquid surface of the liquid present outside the internal container within the external container.

With such a stabilization member disposed, the internal container and the liquid can be stabilized. This ensures that even upon severe vibration, exposure of the lower end of the internal container to air can be prevented, and, therefore, flowing-in of air into the internal container can be obviated.

The disclosure herein also provides an exemplary storage transport method for film-shaped tissue composed of biological cells, the method including a floating step of floating the film-shaped tissue in a storage fluid placed in a container main body of an external container, a containing step of creating a state in which an internal container having a lower opening portion opening downward is mounted on a bottom section of the container main body, the internal container is filled with the storage fluid to such an extent that no gas layer is formed within the internal container, and the film-shaped tissue is contained in a floating state in the internal container; and a sealing step of sealing within the external container the internal container containing the film-shaped tissue therein, by closing the container main body with a lid member of the container main body, in a state where an interposed unit having elasticity is clamped between the lid member and the internal container.

According to the disclosure, it is ensured that even when the storage transport container is vibrated, damaging or breakage of the film-shaped tissue can be obviated, and an operation of taking out the film-shaped tissue can be speedily carried out. Furthermore, even if there are some errors in the shape and/or dimensions of the external container attendant on production accuracy of the external container, the internal container can be fixed within the external container stably and assuredly.

In the storage transport method for film-shaped tissue, preferably, a configuration is adopted wherein the internal container has a liquid-permeable wall section which faces the bottom section of the container main body with a spacing therebetween and is so configured as to permit passage of liquid therethrough, and in the containing step, the internal container is mounted on the bottom section of the container main body, thereby filling the internal container with the storage fluid and floating the film-shaped tissue in the storage fluid within the internal container.

This configuration enables air to be discharged out of the internal container via the liquid-permeable wall section, so that the internal container can be easily filled with a liquid. In addition, flowing-in of air into the internal container via a gap between the internal container and the interposed unit can be obviated.

According to the exemplary embodiments of the film-shaped tissue storage transport container and storage transport method disclosed here, a film-shaped tissue can be easily stored and transported, without damaging the original shape of the film-shaped tissue and while maintaining the quality and biological activity of the film-shaped tissue.

DETAILED DESCRIPTION

A storage transport container and a storage transport method for film-shaped tissue according to the disclosure herein will be described below, showing preferred exemplary embodiments and referring to the accompanying drawings.

Figure 1:
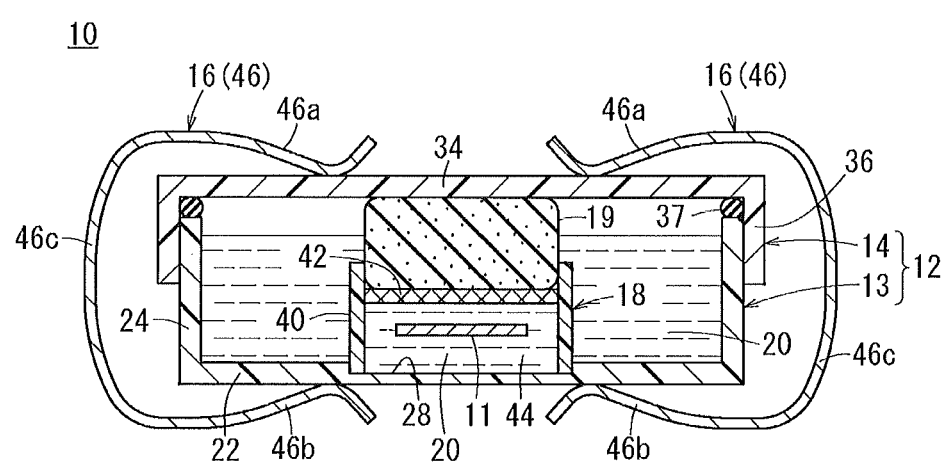
FIG. 1 is a sectional view of a storage transport container for film-shaped tissue according to a first exemplary embodiment of the disclosure.
Figure 2:
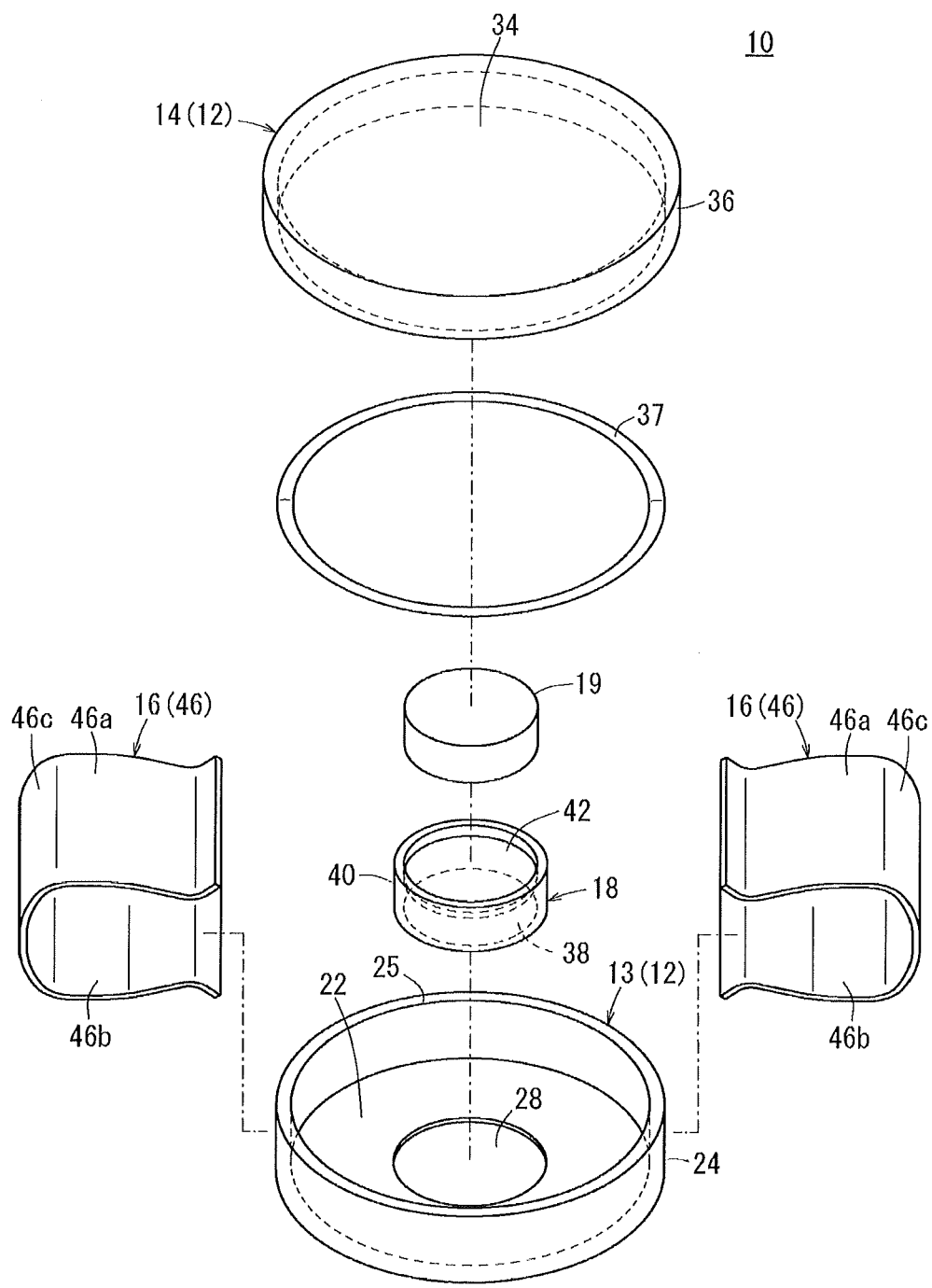
FIG. 2 is an exploded perspective view of the storage transport container shown in FIG. 1.

FIG. 1 is a sectional view of a storage transport container 10 for film-shaped tissue according to a first exemplary embodiment (hereinafter referred to simply as "the storage transport container 10"), and FIG. 2 is an exploded perspective view of the storage transport container 10. The storage transport container 10 is a device to be used for storage or transport of a film-shaped tissue 11 composed of biological cells (living body-derived cells). The storage transport container 10 includes: an external container 12 having a container main body 13 and a lid member 14; a coupling mechanism 16 which couples the container main body 13 and the lid member 14; an internal container 18 disposed inside the external container 12; an interposed unit 19 disposed between the internal container 18 and the lid member 14; and a storage fluid 20 placed in the internal container 18 and the external container 12, with the film-shaped tissue 11 being present in a floating state in the storage fluid 20 with which the internal container 18 is filled.

The film-shaped tissue 11 as an object of storage and transport is a living body-derived structure of a certain extent of thickness that is used, for example, for regeneration, therapy or promotion of healing of a malady, disease or deficit of part or the whole part of an organ or tissue such as heart, cornea, retina, blood vessel, nerve, epidermis, dermis, cartilage, tooth, etc. or of a plurality of organs, or for examination of pungency, sensitization properties or toxicity of drugs to organs or tissues, effects of drugs, reactions of drugs on tissues, etc. Specific examples of the film-shaped tissue 11 include dermal tissue, mucous epithelial tissue, corneal epithelial tissue, cultivated skin, cultivated dermis, cultivated epidermis, cultivated epithelial tissue, cultivated corneal tissue, cartilage tissue, retinal tissue, neurofilament, artificial blood vessel, myoblast tissue, and sheet-shaped cell cultures produced from the aforementioned biological tissue-derived cells. Preferable examples of the film-shaped tissue 11 include sheet-shaped cell cultures composed of myoblast. The film-shaped tissue 11 may be composed only of cells or cell secretions, and may further contain a substance or substances not derived from a living body, such as a support or supports.

The external container 12 is sized so that it can contain the internal container 18 therein. Specifically, the external container 12 is sized so that, in the state where the internal container 18 is contained in the external container 12, a space (for example, an annular space) is formed between the outer circumference of the internal container 18 and the inner circumference of the external container 12. In addition, the external container 12 is preferably sized so that a sufficient operating space can be secured at the time of taking the internal container 18 out of the external container 12 and taking out the film-shaped tissue 11 floating in the storage fluid 20 by use of an appropriate instrument (a graft device, etc.). For instance, where the external container 12 is a circular Petri dish, its inside diameter is preferably about 30 to 300 mm, more preferably about 80 to 150 mm greater than the outer circumference of the internal container 18.

The container main body 13 is a bottomed tube-shaped body (in the illustrated example, a bottomed cylindrical body) which includes a roughly flat plate-shaped bottom section 22 and a side wall section 24 extending upward from an outer circumferential edge portion of the bottom section 22. An upper part of the container main body 13 is open so as to define an upper opening portion 25 (see FIG. 2) that is opening on the upper side.

The bottom section 22 is provided with a shallow groove-shaped position-restricting portion 28 for positioning the internal container 18 in horizontal directions. The position-restricting portion 28 has the function of engaging with the lower end of the internal container 18 to thereby position the internal container 18 in the horizontal directions relative to the container main body 13. The position-restricting portion 28 in the illustrated example is a circular groove (depression) having an inside diameter slightly greater than the outside diameter of the lower end of the internal container 18, and is provided substantially in the center of the bottom section 22. The configuration of the position-restricting portion 28 is not limited to this; for example, the position-restricting portion 28 may be a circular annular groove, or may be projections that project upward at a plurality of positions in the circumferential direction. The position-restricting portion 28 is not an indispensable component; and thus, a configuration may be adopted wherein the position-restricting portion 28 is omitted.

The lid member 14 includes a top section 34, and a side wall section 36 extending downward from an outer circumferential edge portion of the top section 34. The lid member 14 is configured so as to close the upper opening portion 25 of the container main body 13. The inside diameter of the side wall section 36 is roughly equal to or slightly greater than the outside diameter of the side wall section 24 of the container main body 13.

On a lower surface of an outer circumferential portion of the top section 34 is provided an annular seal member 37. When the container main body 13 is closed with the lid member 14, the part between the lid member 14 and the container main body 13 is sealed with the seal member 37, whereby the external container 12 is sealed liquid-tight. Note that instead of providing the seal member 37 on the lower surface of the top section 34 of the lid member 14, the seal member 37 may be provided on an upper surface of the side wall section 24 of the container main body 13, whereby the same sealing effect as aforementioned can be obtained. The seal member 37 is a member for preventing leakage of liquid, and is, for example, formed from silicone or butadiene rubber.

The internal container 18 is a container so sized that the film-shaped tissue 11 can be contained in the internal container 18 in the state of maintaining the size and configuration of the original shape thereof. The internal container 18 is provided with a lower opening portion 38 (see FIG. 2) which opens downward and which is greater than the plan-view shape of the film-shaped tissue 11 to be contained in the internal container 18. In this exemplary embodiment, the internal container 18 includes a tube-shaped section 40 opening upward and downward, and a mesh section 42 provided at an intermediate position in the height direction of the tube-shaped section 40.

The length in the axial direction (the size in the height direction) of the tube-shaped section 40 is shorter than the distance from the bottom section 22 (the position-restricting portion 28) of the container main body 13 to the lid member 14 in the condition where the container main body 13 is closed with the lid member 14. In the state where the container main body 13 is closed with the lid member 14, therefore, the upper end of the tube-shaped section 40 is spaced from the lid member 14. While the tube-shaped section 40 is configured in a cylindrical shape (circular tube shape) in this embodiment, the tube-shaped section 40 may also be formed, for example, in an elliptic tube shape or a polygonal tube shape.

The mesh section 42 is provided at an intermediate position in the axial direction of the tube-shaped section 40, substantially orthogonal to the axial direction. In the condition where the internal container 18 is mounted on the bottom section 22 of the container main body 13, the mesh section 42 faces the bottom section 22 in a substantially parallel relationship. An outer circumferential edge portion of the mesh section 42 is secured to an inner circumferential surface of the tube-shaped section 40 over the entire circumference. In this embodiment, the mesh section 42 faces the bottom section 22 of the container main body 13 with a spacing therebetween, and functions as a liquid-permeable wall section configured to permit passage of liquid therethrough. When the internal container 18 is mounted on the bottom section 22 of the external container 12, the lower opening portion 38 of the internal container 18 is closed with the bottom section 22 of the external container 12, resulting in that a containing chamber 44 for the film-shaped tissue 11 is formed which is surrounded by the tube-shaped section 40, the mesh section 42 and the bottom section 22.

The containing chamber 44 is filled with the storage fluid 20 for the film-shaped tissue 11, to such an extent that no gas layer is formed within the containing chamber 44. In other words, the containing chamber 44 is in the state of being substantially entirely filled with the storage fluid 20 so that no air layer is formed on the upper side within the containing chamber 44. The expression "filled with the storage fluid 20 in such an extent that no gas layer is formed within the containing chamber 44" is used with an understanding that the presence of some foams in an upper portion of the interior of the containing chamber 44 may be permitted. Even when some foams are thus present in an upper portion of the interior of the containing chamber 44, there is little possibility of generation of waving or flowing of the storage fluid 20 within the containing chamber 44 when the storage transport container 10 is vibrated. Examples of the storage fluid 20 include liquid culture medium, physiological salt solution, isotonic solution, buffer solution, Hanks' balanced salt solution, and the like.

The interposed unit 19 is a member having elasticity (expandable and contractable property), and is disposed in an elastically compressed state between the lid member 14 and the internal container 18. In this exemplary embodiment, the interposed unit 19 is composed of a porous body. Examples of the porous body include sponge and nonwoven fabric. In addition, the porous body is of a structure in which adjacent pores communicate with one another and which has a liquid-absorbing property, or may be of a structure in which adjacent pores are independent from each other and which does not have a liquid-absorbing property.

The interposed unit 19 has its upper surface in contact with a lower surface of the lid member 14, and its lower surface in contact with an upper surface of the mesh section 42. The thickness (height dimension) of the interposed unit 19 in a natural state (non-compressed state) is greater than the distance between the mesh section 42 of the internal container 18 disposed inside the outer container 12, of which the container main body 13 is closed with the lid member 14, and the lid member 14. Therefore, the interposed unit 19 is held while being sandwiched between the lid member 14 and the mesh section 42 in an elastically compressed state. An outer circumferential surface on a lower portion side of the interposed unit 19 is in contact with an inner circumferential surface on an upper portion side (the upper side relative to the mesh section 42) of the tube-shaped section 40 of the internal container 18, over the whole circumference.

In the case where the tube-shaped section 40 and the interposed unit 19 are cylindrical as in the illustrated embodiment, it is preferable that the outside diameter of the interposed unit 19 is roughly equal to or slightly greater than the inside diameter of the tube-shaped section 40. This ensures that in the condition where the interposed unit 19 is fitted in the tube-shaped section 40, the outer circumferential surface of the interposed unit 19 securely makes contact with the inner circumferential surface of the tube-shaped section 40 over the entire circumference. Consequently, no gap that permits passage of gas therethrough would be formed between the inner circumferential surface of the tube-shaped section 40 and the outer circumferential surface of the interposed unit 19. The interposed unit 19 is not restricted to the cylindrical shape (circular tube shape); thus, where the tube-shaped section 40 has a non-circular shape (for example, an elliptic tube shape, a polygonal tube shape or the like), the interposed unit 19 can be formed in a non-circular shape corresponding to the shape of the inner circumferential surface of the tube-shaped section 40.

The materials constituting the internal container 18, the container main body 13 and the lid member 14 mentioned above are not particularly limited. Examples of the materials include various resins such as polyvinyl chloride, polyethylene, polypropylene, cyclic polyolefin, polystyrene, poly (4-methylpentene-1), polycarbonate, acrylic resin, acrylonitrile-butadiene-styrene copolymer, polyesters such as polyethylene terephthalate, polyethylene naphthalate, etc., butadiene-styrene copolymer, polyamides (e.g., nylon 6, nylon 6,6, nylon 6,10, nylon 12), glasses, ceramics, metals, and alloys. In addition, the materials constituting the internal container 18, the container main body 13 and the lid member 14 are preferably substantially transparent, for securing inside visibility. Furthermore, the materials preferably have surfaces to which cells are not liable to stick, for the purpose of preventing adhesion of cells thereto.

The material constituting the interposed unit 19 composed of a porous body is not specifically restricted insofar as the material has elasticity (flexibility). Examples of the material include natural materials such as cotton, cotton, gauze, rayon, etc., and synthetic materials such as polyesters, polyamides, PVDF, polyether-sulfones, polysulfones, etc.

In the condition where the container main body 13 is closed with the lid member 14, where the lid member 14 and the container main body 13 are coupled by the coupling mechanism 16, and where the interposed unit 19 is disposed between the internal container 18 and the lid member 14, the internal container 18 is pressed against the container main body 13 by the elastic force of the interposed unit 19. In this condition, therefore, movement of the internal container 18 within the external container 12 is restricted. As a result, the internal container 18 can be stably fixed within the external container 12.

The storage fluid 20 is contained inside the external container 12 and outside the internal container 18 (between the external container 12 and the internal container 18). The storage fluid 20 present inside the external container 12 and outside the internal container 18 (hereinafter referred to also as "the storage fluid 20 on the outside") is present in such an amount that the interposed unit 19 is partly immersed in the storage fluid 20. In other words, the height of the liquid surface of the storage fluid 20 on the outside is set at a position above the mesh section 42 of the internal container 18. The height of the liquid surface of the storage fluid 20 on the outside may exceed the height of the upper end of the internal container 18 (specifically, the tube-shaped section 40), as shown in FIG. 1.

The coupling mechanism 16 is utilized for coupling the container main body 13 to the lid member 14. The coupling mechanism 16 in the illustrated example is composed of two clips 46, each of which makes contact with both the lower surface of the container main body 13 and the upper surface of the lid member 14 and elastically clamps the container main body 13 and the lid member 14. Each of the clips 46 is composed of a pair of arm sections 46*a* and 46*b* extending while facing each other, and an interlock section 46*c* interlocking base end portions of the pair of arm sections 46*a* and 46*b* to each other. Each clip 46 can be opened wider through a process in which the pair of arm sections 46*a* and 46*b* is elastically deformed in respective outward directions. In a natural state (in a state where no external force is exerted on the clip 46), the spacing between the pair of arm sections 46*a* and 46*b* is smaller than the thickness (height) of the external container 12 in the condition where the container main body 13 is closed with the lid member 14. Such clips 46 can be configured by use of any of various metals, alloys, resins, etc. having elasticity.

In FIG. 1, the two clips 46 are attached to the external container 12 at positions on the opposite sides. However, the number of the clips 46 to be attached may be appropriately set within such a range that the lid member 14 and the container main body 13 can be coupled to each other with an appropriate holding force by the clips 46. Therefore, the number of the clip(s) 46 may also be only one, or may be three or more.

The operation and effects of the storage transport container 10 will be described below.

In order to assemble the aforementioned storage transport container 10, the following steps are carried out.

(1) Floating Step

Figure 3A:
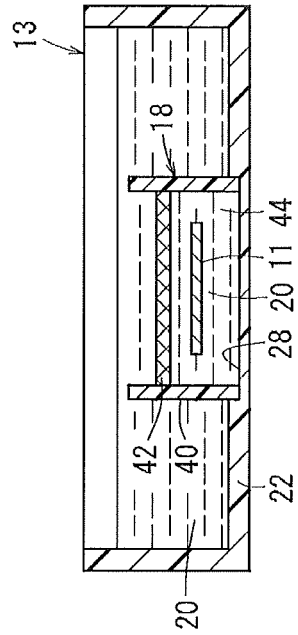
FIG. 3A is a first figure illustrating an assembly method for the storage transport container shown in FIG. 1.

In a floating step, as shown in FIG. 3A, the storage fluid 20 is placed in the container main body 13, and the film-shaped tissue 11 is floated in the storage fluid 20.

(2) Containing Step

A containing step is a step of creating a state wherein the internal container 18 is mounted on the bottom section 22 of the container main body 13, the internal container 18 is filled with the storage fluid 20 in such an extent that no gas layer would be formed within the internal container 18, and the film-shaped tissue 11 is contained in a floating state inside of the internal container 18 (the containing chamber 44).

Figure 3B:
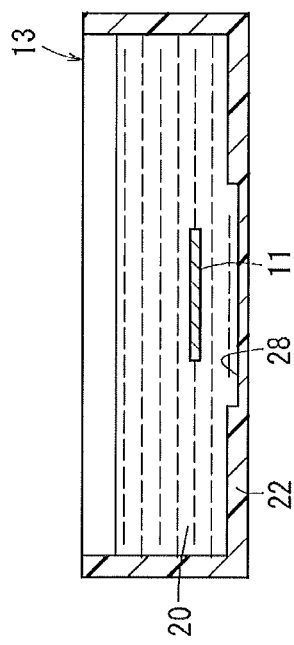
FIG. 3B is a second figure illustrating the assembly method for the storage transport container shown in FIG. 1.

Specifically, as shown in FIG. 3B, the internal container 18 is mounted on the bottom section 22 of the container main body 13 in such a manner that the film-shaped tissue 11 and the storage fluid 20 in the surroundings thereof are covered by the internal container 18. In this case, in this exemplary embodiment, the internal container 18 is mounted on the position-restricting portion 28 formed as part of the bottom section 22. Note that at the stage of FIG. 3A, the storage fluid 20 is introduced while adjusting the fluid amount so that the liquid surface of the storage fluid 20 will be above the mesh section 42 of the internal container 18 when the internal container 18 is mounted on the bottom section 22 of the container main body 13.

In the process of gradually sinking the internal container 18 into the storage fluid 20 in the container main body 13, air present within the internal container 18 is discharged through the mesh section 42 provided as part of the internal container 18, whereby the internal container 18 is filled up with the storage fluid 20. Since the air present in the internal container 18 can thus be discharged through the mesh section 42 and the inside of the internal container 18 can thus be flushed with the storage fluid 20, the internal container 18 can be filled with the storage fluid 20 easily and swiftly.

(3) Sealing Step

A sealing step is a step of closing the container main body 13 with the lid member 14 (see FIG. 3D), in a state where the interposed unit 19 is held while being braced between the lid member 14 and the internal container 18, whereby the internal container 18 with the film-shaped tissue 11 contained therein is sealed in the external container 12.

Figure 3C:
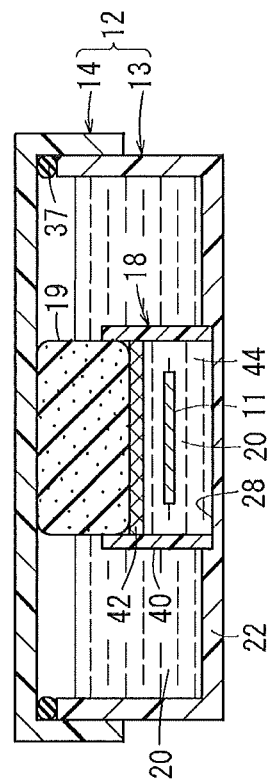
FIG. 3C is a third figure illustrating the assembly method for the storage transport container shown in FIG. 1.
Figure 3D:
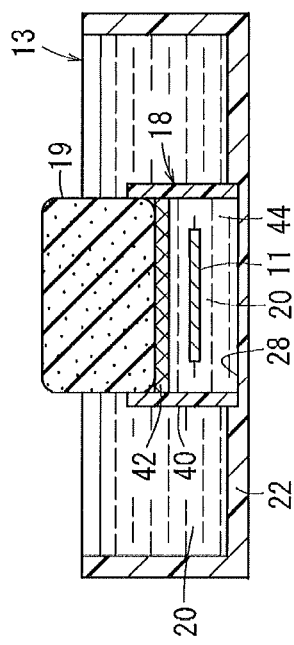
FIG. 3D is a fourth figure illustrating the assembly method for the storage transport container shown in FIG. 1.

In the sealing step, first, the interposed unit 19 is mounted on the internal container 18, as shown in FIG. 3C. Specifically, the interposed unit 19 is inserted through the opening portion on the upper side of the internal container 18, and the bottom surface of the interposed unit 19 is brought into contact with the mesh section 42 of the internal container 18, and the outer circumferential surface of the interposed unit 19 and the inner circumferential surface of the tube-shaped section 40 of the internal container 18 are put in contact with each other over the entire circumference. In the case where the interposed unit 19 is a porous body having a water-absorbing property, part of the storage fluid 20 is absorbed into the interposed unit 19, whereby the interposed unit 19 is put into a wet state.

Next, the container main body 13 is closed with the lid member 14, and the container main body 13 and the lid member 14 are coupled to each other by the aforementioned clips 46. This results in that the internal container 18 is held between the lid member 14 and the container main body 13, with the interposed unit 19 therebetween, so that the internal container 18 is fixed stably within the external container 12.

With the above steps (1) to (3) carried out, the storage transport container 10 in the state as shown in FIG. 1 is completed. Note that the aforementioned operating steps for assembling the storage transport container 10 are carried out, for example, in a clean room, in an operating room, or in an aseptic environment.

In order to take the film-shaped tissue 11 out of the storage transport container 10 in the state shown in FIG. 1, first, the clips 46 are detached to release the lid member 14 and the container main body 13 from the fixed state, after which the lid member 14 is detached from the container main body 13. Next, the interposed unit 19 is removed from the internal container 18, followed by gradually lifting up the internal container 18 relative to the container main body 13. Then, as the internal container 18 is raised, air flows into the internal container 18 through the mesh section 42, so that the film-shaped tissue 11 and the storage fluid 20 having been contained in the internal container 18 are left in the container main body 13.

Note that a procedure may be adopted in which, without removing the interposed unit 19 from the internal container 18, the internal container 18 is lifted up together with the interposed unit 19, whereby the film-shaped tissue 11 in the internal container 18 is transferred to the container main body 13 side together with the storage fluid 20. When the interposed unit 19 is preliminarily removed from the internal container 18 before lifting up the internal container 18 as aforementioned, however, it is ensured that air flows into the internal container 18 through the mesh section 42 and, therefore, the internal container 18 can be lifted up with little flowing or disturbance of the storage fluid 20. Consequently, influences on the film-shaped tissue 11 can be minimized.

After the film-shaped tissue 11 is put into a floating state in the storage fluid 20 inside the container main body 13 by the aforementioned method, the film-shaped tissue 11 is taken out of the storage fluid 20 by use of an appropriate instrument (a graft device, etc.), and is provided to the intended therapy, such as transplantation into a patient.

According to the storage transport container 10 of the exemplary embodiment disclosed above, the internal container 18 is filled with the storage fluid 20, and the film-shaped tissue 11 is set floating in the storage fluid 20. Therefore, even if the storage transport container 10 is vibrated during transport to cause vibration of the internal container 18, the storage fluid 20 inside the internal container 18 is prevented from waving or flowing. Accordingly, the vibration is not transmitted to the film-shaped tissue 11, so that breakage of the film-shaped tissue 11 can be prevented.

In this embodiment, the internal container 18 has the lower opening portion 38, and the lower end of the internal container 18 comes into contact with the bottom section 22 of the external container 12, whereby the lower opening portion 38 is closed. At the time of an operation of taking out the film-shaped tissue 11, therefore, simple lifting-up of the internal container 18 relative to the container main body 13 causes the film-shaped tissue 11 having been contained in the internal container 18 to move to the container main body 13 side. Accordingly, it is unnecessary to transfer the film-shaped tissue 11 and the storage fluid 20 into another container. Consequently, the operation can be carried out speedily, and the risk of breaking the film-shaped tissue 11 during a transferring operation can essentially be avoided.

In this embodiment, the storage fluid 20 is contained outside the internal container 18. This ensures that air can be prevented from flowing into the internal container 18 through the lower opening portion 38 of the internal container 18. To be more specific, in the case where the storage fluid 20 is absent on the outside of the internal container 18, the storage fluid 20 present inside the internal container 18 may leak out through a part between the internal container 18 and the bottom section 22 of the container main body 13, causing air to flow into the internal container 18. With the storage fluid 20 present in the surroundings of the internal container 18, however, such flowing-in of air is inhibited.

Note that in assembly of the storage transport container 10, a procedure may be adopted in which the air present inside the internal container 18 is discharged, the internal container 18 is mounted on the bottom section 22 of the container main body 13, thereafter the storage fluid 20 present outside the internal container 18 is removed, and a gel-formed material is introduced in place of the storage fluid 20. In this case, the presence of the gel-formed material in the surroundings of the internal container 18 can prevent gas from flowing into the internal container 18 through the lower opening portion 38. In addition, the internal container 18 is held by the gel-formed material, whereby the internal container 18 is inhibited from moving, so that the internal container 18 can be fixed more stably.

In this exemplary embodiment, the interposed unit 19 is provided on top of the internal container 18; in addition, the interposed unit 19 is held in an elastically compressed state between the internal container 18 and the lid member 14 when the container main body 13 is closed with the lid member 14 and they are fixed by the clips 46. The internal container 18 is pressed against the container main body 13 by the elastic force of the interposed unit 19. Accordingly, the internal container 18 is stably fixed within the external container 12.

Since the internal container 18 is thus stably fixed inside the external container 12, the internal container 18 is prevented from being shifted within the external container 12. In addition, the lower end of the internal container 18 is prevented from floating up from the bottom section 22 of the container main body 13, and the state in which the internal container 18 is filled with the storage fluid 20 can be maintained in a favorable manner. The position-restricting portion 28 prevents the internal container 18 from being shifted sideways relative to the container main body 13, so that the film-shaped tissue 11 can be stably held.

Even if the external container 12 involves some shape errors or dimensional errors arising from accuracy of production, such errors can be absorbed by the elasticity (expandable and contractable property) of the interposed unit 19; therefore, the internal container 18 can be fixed within the external container 12 stably and assuredly. Specifically, the interposed unit 19 is compressed to an appropriate extent according to the distance between the lid member 14 and the mesh section 42 of the internal container 18, whereby the internal container 18 can be assuredly pressed against the container main body 13. Accordingly, the dimensional restrictions and production accuracy required of the external container 12 are moderated, so that a reduction in production cost can be promised.

In this exemplary embodiment, the outer circumferential surface of the interposed unit 19 and the inner circumferential surface of the tube-shaped section 40 are in contact with each other over the whole circumference. Therefore, flowing-in of air into the internal container 18 through a gap between the outer circumferential surface of the interposed unit 19 and the inner circumferential surface of the tube-shaped section 40 is inhibited, so that a liquid-tight state inside the internal container 18 (the containing chamber 44) is maintained. Even in the case where the interposed unit 19 has a structure in which adjacent pores communicate with one another, air is prevented from flowing into the internal container 18 via the pores in the interposed unit 19, since the interposed unit 19 has absorbed the storage fluid 20.

In the case of this exemplary embodiment, at the time of filling the internal container 18 with the storage fluid 20 in the assembly process of the storage transport container 10, air can be discharged from the internal container 18 through the mesh section 42 serving as a liquid-permeable wall section. Therefore, the internal container 18 can be easily filled with the storage fluid 20. Especially, according to the mesh section 42, a large flow path area for passage of the storage fluid 20 therethrough can be secured, whereby an excellent liquid passing property is offered. Therefore, it is possible to reduce the fluid resistance at the mesh section 42 during the process of discharging the air from the internal container 18 and further sinking the internal container 18 into the storage fluid 20. Accordingly, the internal container 18 can be speedily mounted on the bottom section 22 of the container main body 13.

In this exemplary embodiment, the coupling mechanism 16 is composed of the clips 46. Therefore, even in the case where the external container 12 is formed from a comparatively easily bendable material such as a resin material, the internal container 18 can be assuredly pressed against the container main body 13 by the lid member 14, through clamping them from the upper surface and the lower surface of the external container 12. As a result, the internal container 18 can be fixed more stably. Note that in the case where the coupling mechanism 16 is composed of the clips 46, it is preferable that distal portions of the arm sections 46a and 46b (the portions for contact with the external container 12) of the clips 46 clamp therebetween the portions where the internal container 18 and the interposed unit 19 make contact with the external container 12.

Figure 4A:
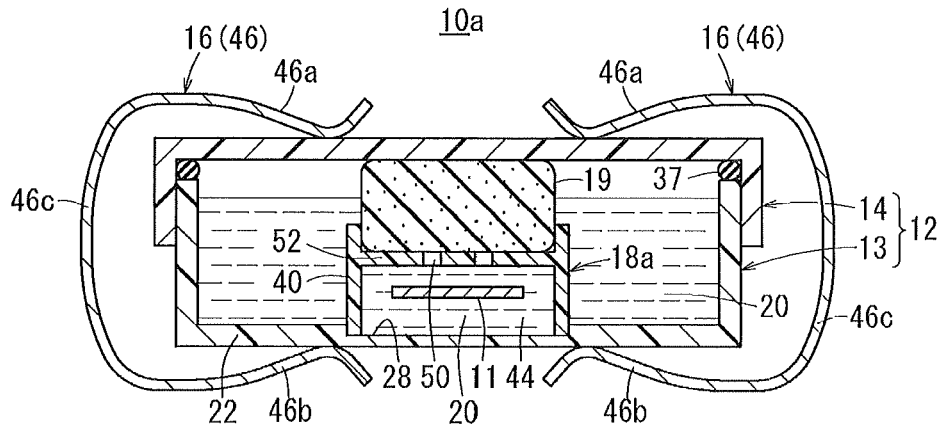
FIG. 4A is a sectional view of a storage transport container for film-shaped tissue according to a first modification of the first exemplary embodiment.

An internal container 18a having a top wall 52 provided with through-holes 50, as in a storage transport container 10a according to a first modification illustrated in FIG. 4A, may be adopted in place of the aforementioned internal container 18 having the mesh section 42. The top wall 52 is provided at an intermediate position in the axial direction of the tube-shaped section 40, substantially orthogonally to the axial direction. In the state where the internal container 18a is mounted on the bottom section 22 of the container main body 13, the top wall 52 faces the bottom section 22 in a substantially parallel relationship. The through-holes 50 are so formed as to offer communication between the inside and the outside of the internal container 18a. While the through-holes 50 are provided in plurality in FIG. 4A, a configuration may be adopted in which only one through-hole 50 is provided. The top wall 52 configured in this way faces the bottom section 22 of the container main body 13, with a spacing therebetween, and functions as a liquid-permeable wall section permitting passage of liquid therethrough. The top wall 52 may be formed integrally with the tube-shaped section 40, or may be produced as a component part separate from the tube-shaped section 40 and be joined to the tube-shaped section 40.

The lower surface of the interposed unit 19 and the upper surface of the top wall 52 are in secure contact with each other, and the through-holes 50 are closed with the interposed unit 19. Therefore, the storage fluid 20 present between the internal container 18a and the external container 12 is prevented from flowing into the internal container 18a through a gap between the interposed unit 19 and the top wall 52. Accordingly, a liquid-tight state inside the internal container 18a is maintained.

The storage transport container 10a configured as above-described can be assembled by a procedure equivalent or similar to that for the storage transport container 10 described above. In the case of the storage transport container 10a, in the process of gradually sinking the internal container 18a into the storage fluid 20 within the container main body 13, air present inside the internal container 18a is discharged through the through-holes 50 provided in the top wall 52 of the internal container 18a. As a result, the internal container 18a is filled up with the storage fluid 20.

The storage transport container 10a according to the first modification illustrated in FIG. 4A thus has a configuration wherein the interposed unit 19 is mounted directly on the top wall 52. Alternatively, a configuration may be adopted wherein a closing member 54 is disposed between the top wall 52 and the interposed unit 19, as in a storage transport container 10b according to a second modification illustrated in FIG. 4B. The closing member 54 includes a closing plate 56 whose lower surface is put into surface contact with the upper surface of the top wall 52, and a hand grip 58 projected upward from an end portion of the closing plate 56. In a state where the closing member 54 is sandwiched between the top wall 52 and the interposed unit 19, the through-holes 50 are closed with the closing plate 56. The hand grip 58 is a portion gripped by the user at the time of mounting the closing member 54 onto the top wall 52 of the internal container 18a and at the time of lifting up the closing member 54.

According to the storage transport container 10b thus configured, the through-holes 50 are closed with the closing member 54. Therefore, flowing-in of air into the internal container 18a through the through-holes 50 can be prevented more securely. Accordingly, a liquid-tight state inside the internal container 18a can be secured in a favorable manner.

Figure 4B:
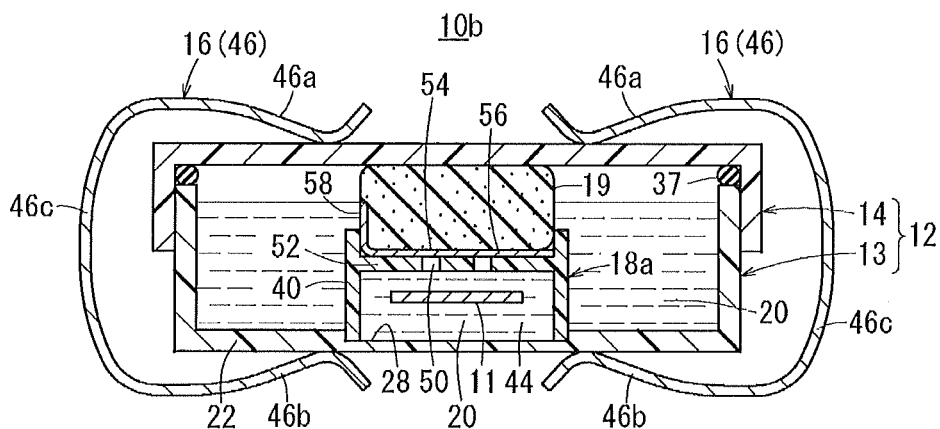
FIG. 4B is a sectional view of a storage transport container for film-shaped tissue according to a second modification of the first exemplary embodiment.

In the storage transport container 10b illustrated in FIG. 4B, the comparatively small through-holes 50 have been provided in plurality. Alternatively, a configuration may be adopted wherein a comparatively large single through-hole 60 is provided, as in a storage transport container 10c illustrated in FIG. 4C. Even in the case where such a large through-hole 60 is provided, the closing member 54 is pressed against the top wall 52 by an elastic force of the interposed unit 19, whereby the upper surface of the top wall 52 and the lower surface of the closing member 54 are put in secure contact with each other, and the through-hole 60 is thereby closed. Consequently, flowing-in of air into an internal container 18b through a gap between the top wall 52 and the closing member 54 can be effectively inhibited.

Figure 5A:
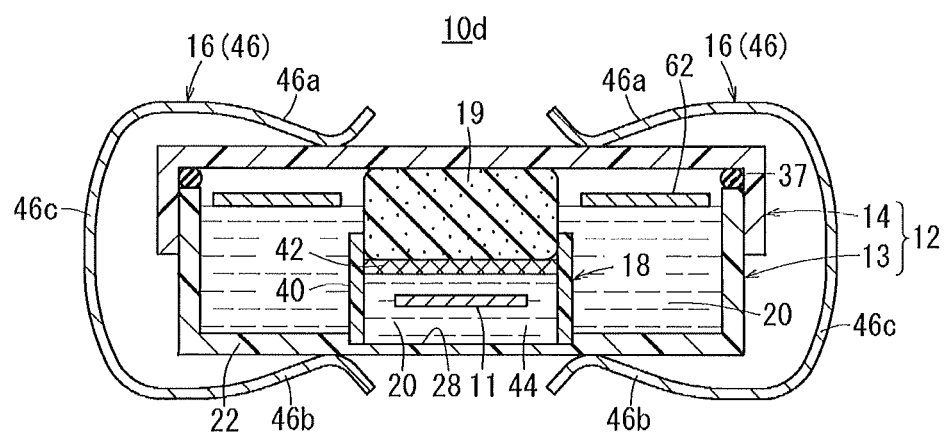
FIG. 5A is a sectional view of a storage transport container for film-shaped tissue according to a fourth modification of the first exemplary embodiment.

In the aforementioned storage transport container 10, air is present on top of the storage fluid 20 existing outside the internal container 18 within the external container 12. When the storage transport container 10 is vibrated, therefore, motion such as waving of the liquid surface of the storage fluid 20 under consideration would be generated. This results in, depending on the severity of the waving or the like, a fear of momentary exposure of the lower end of the external container 12 to the air. In view of this, a stabilization member 62 floating on the liquid surface of the storage fluid 20 present outside the internal container 18 within the external container 12 may be disposed, as in a storage transport container 10d according to a fourth modification of the first exemplary embodiment illustrated in FIG. 5A.

Such a stabilization member 62 may be composed of polystyrene foam or film shaped correspondingly to the shape (in this embodiment, an annular shape) of the area between the internal container 18 and the external container 12. The stabilization member 62 can assume a shape (for example, an annular shape having a certain thickness) corresponding to the shape of a space, exclusive of the storage fluid 20, between the internal container 18 and the external container 12. With such a stabilization member 62 disposed, the internal container 18 and the storage fluid 20 can be stabilized. This ensures that, even upon severe vibration, exposure of the lower end of the external container 12 to air can be prevented from occurring, so that flowing-in of air into the internal container 18 can be prevented.

Figure 4C:
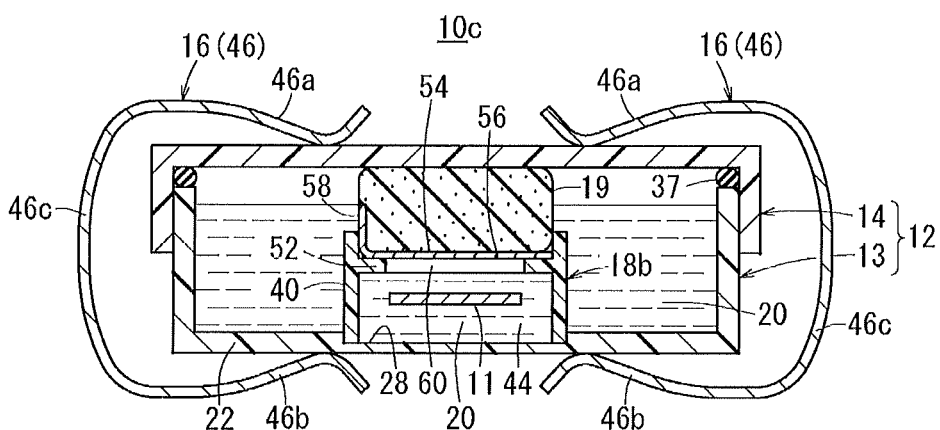
FIG. 4C is a sectional view of a storage transport container for film-shaped tissue according to a third modification of the first exemplary embodiment.

Note that in the storage transport container 10d, the internal container 18a shown in FIG. 4A or the internal container 18b shown in FIG. 4C may be applied in place of the internal container 18. Furthermore, the closing member 54 shown in FIGS. 4B and 4C may be added.

Figure 5B:
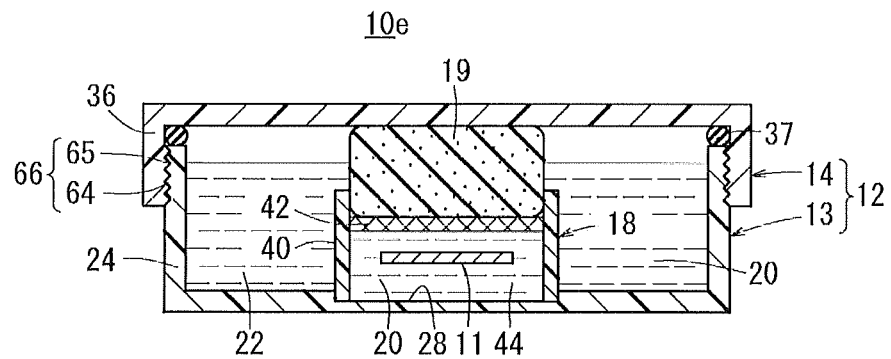
FIG. 5B is a sectional view of a storage transport container for film-shaped tissue according to a fifth modification of the first exemplary embodiment.

In place of the coupling mechanism 16 composed of the plurality of clips 46, there may be adopted a coupling mechanism 66 composed of a male screw section 64 and a female screw section 65 capable of screw engagement with each other, as in a storage transport container 10e according to a fifth modification illustrated in FIG. 5B. The male screw section 64 is formed at an outer circumferential surface of an upper portion of the side wall section 24 of the container main body 13. The female screw section 65 is formed at an inner circumferential surface of the side wall section 36 of the lid member 14. When the female screw section 65 of the lid member 14 is screw engaged with the male screw section 64 of the container main body 13, the lid member 14 and the container main body 13 are securely coupled to each other, and the external container 12 is hermetically closed with the seal member 37 clamped between the lid member 14 and the container main body 13. Using the coupling mechanism 66 configured in this way, the container main body 13 and the lid member 14 can be coupled to each other more speedily by an easier operation, as compared with the coupling mechanism 16 (see FIG. 1, etc.) composed of the clips 46.

Note that in the storage transport container 10e, the internal container 18a shown in FIG. 4A or the internal container 18b shown in FIG. 4C may be applied in place of the internal container 18. Furthermore, the closing member 54 shown in FIGS. 4B and 4C may be provided. In addition, in the storage transport container 10e, the stabilization member 62 shown in FIG. 5A may also be provided.

As the coupling means for coupling the container main body 13 and the lid member 14 to each other, there may be adopted other configurations than the above-mentioned coupling mechanisms 16 and 66. For instance, a coupling mechanism may be adopted which includes an engaging piece provided on one of the container main body 13 and the lid member 14, and a claw section provided on the other of the container main body 13 and the lid member 14, the claw section being caught on the engaging piece to thereby achieve coupling between the container main body 13 and the lid member 14.

Figure 6:
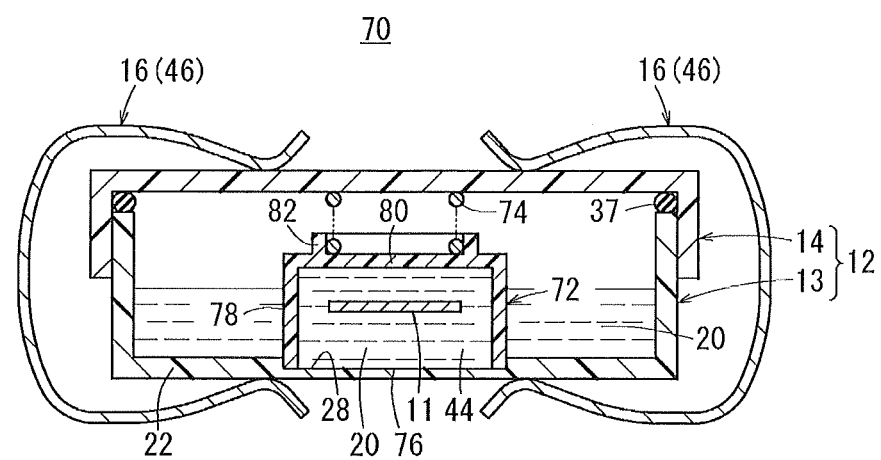
FIG. 6 is a sectional view of a storage transport container for film-shaped tissue according to a second exemplary embodiment of the disclosure.

FIG. 6 is a sectional view of a storage transport container 70 according to a second exemplary embodiment of the disclosure herein. Note that in the storage transport container 70 according to the second embodiment, elements showing functions and effects which are the same as or similar to the functions and effects of the elements in the storage transport container 10 according to the first embodiment described above are denoted by the same reference symbols as used above, and detailed descriptions of such elements will be omitted.

The storage transport container 70 according to the second embodiment differs from the storage transport container 10 according to the first embodiment in the configurations of an internal container 72 and an interposed unit 74. The internal container 72 is a container so sized that the film-shaped tissue 11 can be contained in the internal container 72 in the state of keeping the size and configuration of the original shape thereof. The internal container 72 is provided with a lower opening portion 76 which opens downward and which is greater than the plan-view shape of the film-shaped tissue 11 to be contained in the internal container 72. In this embodiment, the internal container 72 includes a hollow tube-shaped section 78, and a top section 80 provided at the upper end of the tube-shaped section 78. The upper end of the tube-shaped section 78 is closed with the top section 80.

The top section 80 is provided substantially orthogonally to the axial direction of the tube-shaped section 78. In the condition where the internal container 72 is mounted on a bottom section 22 of a container main body 13, the top section 80 faces the bottom section 22 in a substantially parallel relationship. When the internal container 72 is mounted on the bottom section 22 of an external container 12, the lower opening portion 76 of the internal container 72 is closed with the bottom section 22 of the external container 12. As a result, a containing chamber 44 for the film-shaped tissue 11 is formed, which is surrounded by the tube-shaped section 78, the top section 80 and the bottom section 22. The containing chamber 44 is filled with a storage fluid 20, and the film-shaped tissue 11 is present in a floating state in the storage fluid 20.

Between the internal container 72 and a lid member 14 is disposed the interposed unit 74 which has elasticity (expandable and contractable property). The upper end of the interposed unit 74 makes contact with a lower surface of the lid member 14, whereas the lower end of the interposed unit 74 makes contact with an upper surface of the top section 80 of the internal container 72, and the internal container 72 is pressed against the bottom section 22 of the container main body 13 by an elastic force of the interposed unit 74. The length (height size) of the interposed unit 74 in a natural state (non-compressed state) is greater than the distance between the lid member 14 and the top section 80 of the internal container 72 disposed inside the external container 12 in the state where the container main body 13 is closed with the lid member 14. Therefore, the interposed unit 74 is held while being braced in an elastically compressed state between the lid member 14 and the top section 80.

While the interposed unit 74 shown in FIG. 6 is a compression spring in the form of a coil spring, the interposed unit 74 may be a sponge body or a rubber-made spring. In addition, the interposed unit 74 may be fixed to an upper portion (top section 80) of the internal container 72 or a lower surface of the lid member 14, or may be a member independent (separable) from the internal container 72 and the lid member 14.

In order to prevent an erroneous shifting of the interposed unit 74, a position-restricting portion 82 is provided at an upper surface of the top section 80 of the internal container 72. The position-restricting portion 82, in the example shown in FIG. 6, is an annular projection greater in diameter than the interposed unit 74 which is in the form of a coil spring. The position-restricting portion 82, however, may be an annular groove having the same diameter as the annular projection, or may be an annular projection or annular groove which is smaller in diameter than the interposed unit 74. It suffices for the position-restricting portion 82 to have the function of preventing the interposed unit 74 from erroneously shifting. Examples of other forms of the position-restricting portion 82 include a plurality of projections formed at intervals on the upper surface of the top section

80. The position-restricting portion 82 may be provided at the lower surface of the lid member 14.

The height of the liquid surface of the storage fluid 20 present between the internal container 72 and the external container 12 (on the outside of the internal container 72 within the external container 12) is preferably lower than the height of the storage fluid 20 within the internal container 72. This ensures that the atmospheric pressure generates a force which presses the internal container 72 against the bottom section 22 of the container main body 13, so that the internal container 72 can be fixed to the container main body 13 more stably. In place of the storage fluid 20 on the outside of the internal container 72, a liquid different from the storage fluid 20 or a gel-formed material may be contained.

Figure 7A:
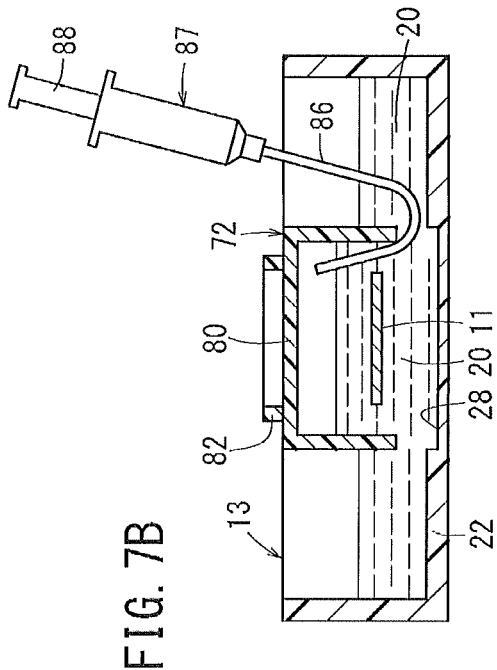
FIG. 7A is a first figure illustrating an assembly method for the storage transport container shown in FIG. 6.
Figure 7B:
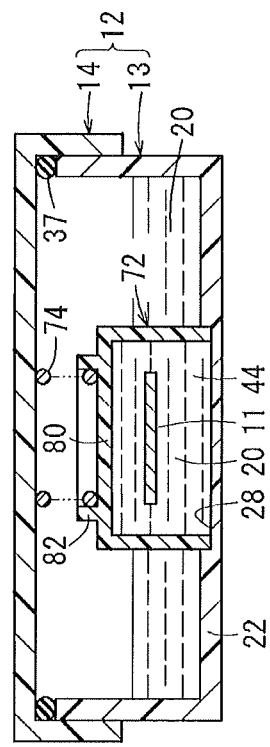
FIG. 7B is a second figure illustrating the assembly method for the storage transport container shown in FIG. 6.

In order to assemble the storage transport container 70 as above, first, the storage fluid 20 is placed in the container main body 13 and the film-shaped tissue 11 is set floating in the storage fluid 20, as illustrated in FIG. 7A. Next, as shown in FIG. 7B, the internal container 72 is disposed in such a manner that the film-shaped tissue 11 and the storage fluid 20 in the surroundings thereof are covered with the internal container 72, that the whole circumference of the lower end of the internal container 72 is located in the storage fluid 20, and that the whole circumference of the lower end of the internal container 72 is spaced from the bottom section 22 of the container main body 13. Then, in this condition, gas (air) present within the internal container 72 is discharged by using, for example, a suction tool 87 (in the illustrated example, a syringe) having a curved nozzle 86 (tube-shaped member).

Specifically, the curved nozzle 86 is inserted into the inside of the internal container 72 through a gap between the lower end of the internal container 72 and the bottom section 22 of the container main body 13, after which a pusher 88 of the suction tool 87 is withdrawn, whereby the gas present in the internal container 72 is sucked. In this instance, bubbles are left inside the internal container 72 at a final stage of the sucking. The bubbles, however, can be substantially completely removed from the inside of the internal container 72 by tilting the internal container 72 to move the bubbles into a corner zone, then locating a distal portion of the nozzle 86 in the corner zone, and performing the sucking operation. In the case where the internal container 72 is composed of a transparent member, the afore-mentioned operation can be carried out while visually confirming the presence of and the position of the bubbles, so that removal of the bubbles can be performed speedily and assuredly.

Figure 7C:
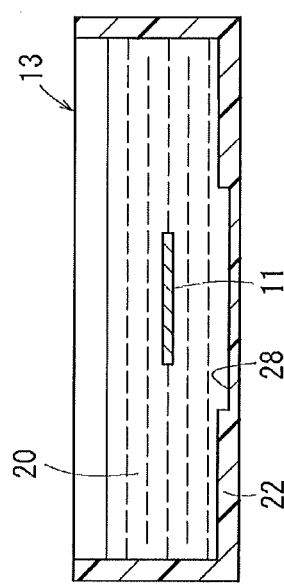
FIG. 7C is a third figure illustrating the assembly method for the storage transport container shown in FIG. 6.

After the gas is removed from the inside of the internal container 72 and the internal container 72 is filled with the storage fluid 20, the internal container 72 is mounted on the bottom section 22 of the container main body 13, as shown in FIG. 7C. In this instance, if the height of the liquid surface of the storage fluid 20 on the outside of the internal container 72 is higher than the height of the storage fluid 20 inside the internal container 72, the amount of the storage fluid 20 on the outside of the internal container 72 is reduced so that the height of the liquid surface of the storage fluid 20 on the outside of the internal container 72 will be lower than the height of the liquid surface of the storage fluid 20 inside the internal container 72.

Figure 7D:
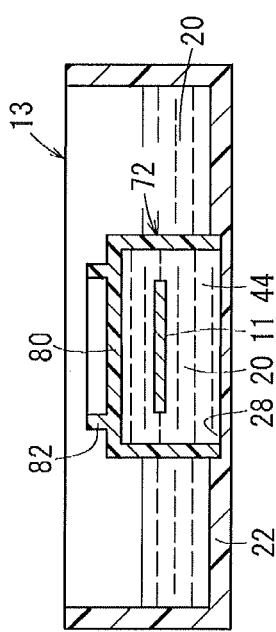
FIG. 7D is a fourth figure illustrating the assembly method for the storage transport container shown in FIG. 6.

Then, in the condition where the interposed unit 74 is sandwiched between the internal container 72 and the lid member 14, the container main body 13 is closed with the lid member 14 (see FIG. 7D), and the container main body 13 and the lid member 14 are coupled to each other by the aforementioned clips 46. As a result, the internal container 72 is pressed against the bottom section 22 of the container main body 13 by the elastic force of the interposed unit 74, so that the internal container 72 is stably fixed within the external container 12. By the above-mentioned operations, the storage transport container 70 shown in FIG. 6 is completed. Note that the above-mentioned operating steps for assembling the storage transport container 70 are carried out in a clean room (in an aseptic environment).

In order to take out the film-shaped tissue 11 from the storage transport container 70 in the state shown in FIG. 6, first, the clips 46 are removed to thereby release the lid member 14 and the container main body 13 from the fixed state, followed by detaching the lid member 14 from the container main body 13. Next, the internal container 72 is lifted up relative to the container main body 13, whereby the film-shaped tissue 11 located inside the internal container 72 is transferred to the container main body 13 side together with the storage fluid 20. Note that when the storage fluid 20 is supplemented to the outside of the internal container 72 to cause the height of the liquid surface of the storage fluid 20 on the outside of the internal container 72 to become higher than the height of the liquid surface of the storage fluid 20 inside the internal container 72, before lifting up the internal container 72 relative to the container main body 13, the lifting-up of the internal container 72 is facilitated owing to buoyancy.

In place of the transferring method as above-mentioned, the following method may be adopted. In the condition where the internal container 72 is lifted up to such an extent that the lower end of the internal container 72 is not completely exposed out of the storage fluid 20 present inside the container main body 13, the curved nozzle 86 of the suction tool 87 shown in FIG. 7B may be inserted into the inside of the internal container 72 through a gap between the lower end of the internal container 72 and the bottom section 22 of the container main body 13, and air may be supplied into the inside of the internal container 72, thereby discharging the storage fluid 20 from the internal container 72. When this procedure is adopted, the internal container 72 can be detached from the container main body 13 without causing any strong flowing motion of the storage fluid 20, so that the risk of breaking the film-shaped tissue 11 by flowing motion of the storage fluid 20 can be eliminated.

According to the storage transport container 70 in this embodiment, the internal container 72 is filled with the storage fluid 20, and the film-shaped tissue 11 is made to float in the storage fluid 20. This ensures that even if vibration is generated during transport of the storage transport container 70 and the internal container 72 is vibrated, the storage fluid 20 inside the internal container 72 is prevented from waving or flowing motion. Therefore, the vibration is not transmitted to the film-shaped tissue 11, so that the film-shaped tissue 11 can be prevented from being broken.

In addition, the interposed unit 74 disposed between the lid member 14 and the internal container 72 has an expandable and contractable property. This ensures that even when some errors exist in the shape or dimensions of the external container 12 due to production accuracy of the external container 12, the errors can be absorbed by the expandable and contractable property of the interposed unit 74. Specifically, the interposed unit 74 is compressed according to the distance between the lid member 14 and the top section 80 of the internal container 72, whereby the internal container 72 can be pressed against the container main body 13 in an assured manner. Consequently, the dimensional limitations and production accuracy in regard of the external container 12 are moderated, so that a reduction in production cost can be promised.

Concerning the components which are common to the first and second embodiments, the same or similar functions and effects to those offered by the common components in the first embodiment can naturally be obtained also in the second embodiment.

Figure 8:
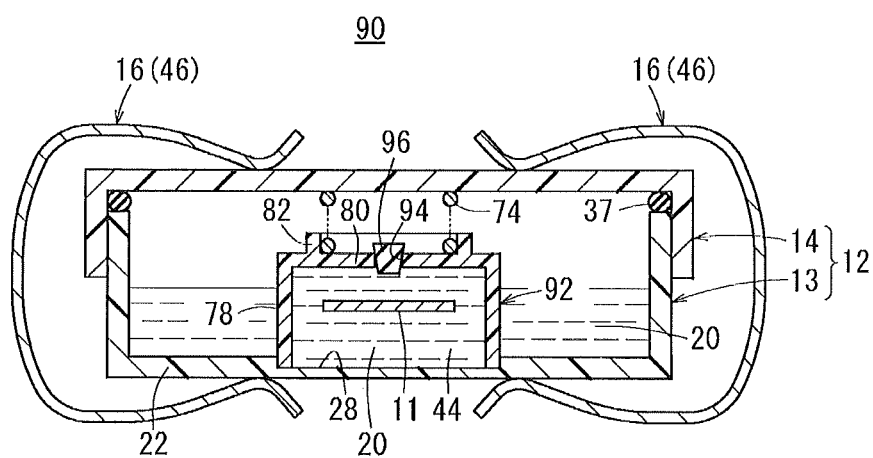
FIG. 8 is a sectional view of a storage transport container for film-shaped tissue according to a third exemplary embodiment of the disclosure.

FIG. 8 is a sectional view of a storage transport container 90 according to a third exemplary embodiment of the disclosure. Note that in the storage transport container 90 according to the third embodiment, elements showing functions and effects which are the same as or similar to the functions and effects of the elements in the storage transport containers 10 and 70 according to the first and second exemplary embodiments described above are denoted by the same reference symbols as used above, and detailed descriptions of such elements will be omitted.

The storage transport container 90 according to the third exemplary embodiment differs from the storage transport container 70 according to the second exemplary embodiment in the configuration of an internal container 92. Specifically, a top section 80 of the internal container 92 is formed with a through-hole 94, and the through-hole 94 is closed with a closing member 96. In the illustrated example, the closing member 96 is, for example, a truncated cone-shaped plug formed from a rubber material. The configuration including the through-hole 94 and the closing member 96 in the illustrated example may be replaced by a configuration wherein a cylindrical projection projecting upward is provided at an upper portion of the through-hole 94, and a cylindrical cap (closing member) opening downward and closed at an upper portion thereof is attached to the projection to achieve closure.

Figure 9A:
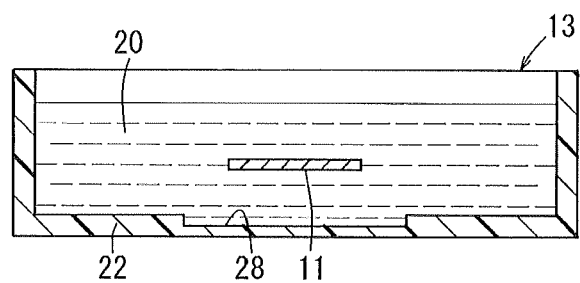
FIG. 9A is a first figure illustrating an assembly method for the storage transport container shown in FIG. 8.
Figure 9B:
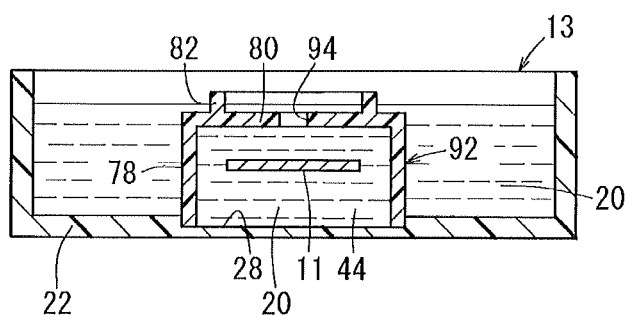
FIG. 9B is a second figure illustrating the assembly method for the storage transport container shown in FIG. 8.

In order to assemble the storage transport container 90 as above-mentioned, first, a storage fluid 20 is placed in a container main body 13, and the film-shaped tissue 11 is made to float in the storage fluid 20, as shown in FIG. 9A. Next, as shown in FIG. 9B, the internal container 92 is mounted on a bottom section 22 of the container main body 13 in such a manner that the film-shaped tissue 11 and the storage fluid 20 in the surroundings thereof are covered with the internal container 92. Note that at the stage of FIG. 9A, the storage fluid 20 is preliminarily introduced while adjusting its amount so that the liquid surface of the storage fluid 20 will be higher than the top section 80 of the internal container 92 when the internal container 92 is mounted on the bottom section 22 of the container main body 13.

Since the top section 80 of the internal container 92 is provided with the through-hole 94, it is ensured that in the process of gradually sinking the internal container 92 into the storage fluid 20 present inside the container main body 13, air in the internal container 92 is discharged via the through-hole 94, and the internal container 92 is filled up with the storage fluid 20. Since the air in the internal container 92 can thus be discharged via the through-hole 94, the inside of the internal container 92 can be filled up with the storage fluid 20 easily and speedily. If necessary, the air in the internal container 92 can be discharged by use of a suction tool 87 (see FIG. 7B) having a nozzle 86.

Figure 9C:
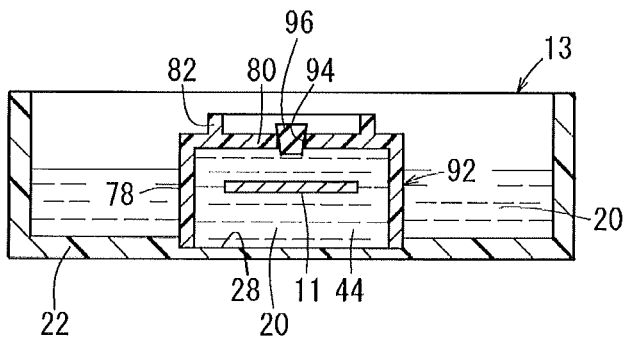
FIG. 9C is a third figure illustrating the assembly method for the storage transport container shown in FIG. 8.

Next, as shown in FIG. 9C, the through-hole 94 is closed with the closing member 96, and the amount of the storage fluid 20 present on the outside of the internal container 92 within the container main body 13 is adjusted to lower the liquid surface of this storage fluid 20 in such a manner that the height of the liquid surface of the storage fluid 20 on the outside of the internal container 92 within the container main body 13 will be lower than the height of the liquid surface of the storage fluid 20 present inside the internal container 92. The storage fluid 20, if any, having entered an interposed unit 74 is removed, as required.

Figure 10A:
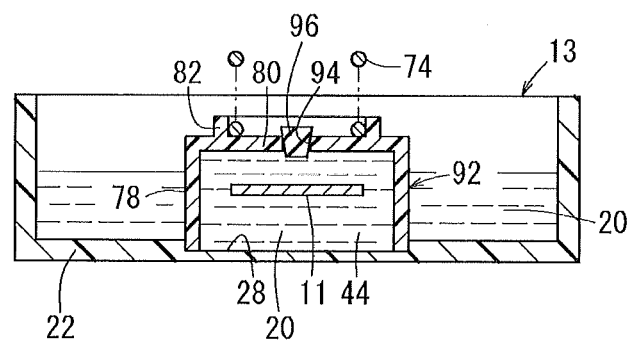
FIG. 10A is a fourth figure illustrating the assembly method for the storage transport container shown in FIG. 8.
Figure 10B:
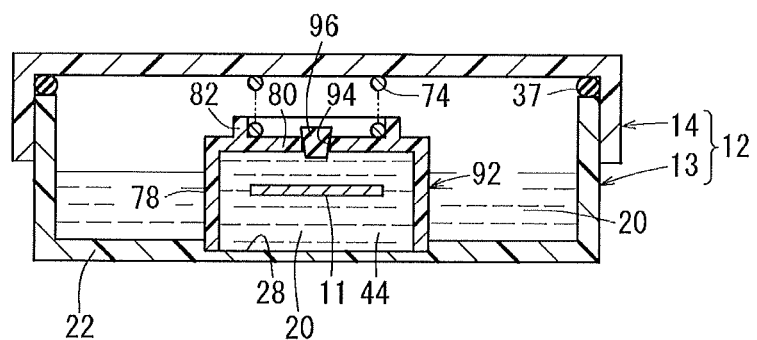
FIG. 10B is a fifth figure illustrating the assembly method for the storage transport container shown in FIG. 8.

Subsequently, as shown in FIG. 10A, the interposed unit 74 is mounted on the internal container 92. Then, as shown in FIG. 10B, the container main body 13 is closed with a lid member 14 (see FIG. 10B), and the container main body 13 and the lid member 14 are coupled to each other by the aforementioned clips 46. This results in that the internal container 92 is clamped between the lid member 14 and the container main body 13 through the interposed unit 74, and, therefore, the internal container 92 is stably fixed within an external container 12. By the operations as above-mentioned, the storage transport container 90 shown in FIG. 8 is completed. Note that the above-mentioned operating steps for assembling the storage transport container 90 are carried out in a clean room (in an aseptic environment).

In order to take out the film-shaped tissue 11 from the storage transport container 90 in the state illustrated in FIG. 8, first, the clips 46 are removed to release the lid member 14 and the container main body 13 from the fixed state, followed by detaching the lid member 14 from the container main body 13. Next, the closing member 96 is detached from the through-hole 94, after which the internal container 92 is gradually lifted up relative to the container main body 13. As the internal container 92 is raised, air flows into the internal container 92 via the through-hole 94, so that the film-shaped tissue 11 and the storage fluid 20 having been contained in the internal container 92 are left inside the container main body 13. After the state wherein the film-shaped tissue 11 is set floating in the storage fluid 20 within the container main body 13 is thus established, the film-shaped tissue 11 is taken out of the storage fluid 20 by use of an appropriate instrument (a graft device, etc.), and is served to therapy such as transplantation into a patient.

Note that concerning the components in the third exemplary embodiment which are common to the first, second and third exemplary embodiments, the same or similar functions and effects to those offered by the common components in the first exemplary embodiment can naturally be obtained also in the third exemplary embodiment.

While the disclosure herein has been described above by showing the preferred exemplary embodiments thereof, the disclosure is not restricted to the above embodiments, and, naturally, various alterations are possible within the scope of the gist of the invention.

The detailed description above describes a film-shaped tissue storage transport container and storage transport method disclosed by way of example. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A storage transport container for film-shaped tissue, to be used for storage or transport of a film-shaped tissue composed of biological cells, the storage transport container comprising:
    an external container that includes a container main body having an upper opening portion opening upward, and a lid member configured to close the upper opening portion of the container main body;

a coupling mechanism coupling the container main body and the lid member;

an internal container disposed inside the external container, having a lower opening portion being greater than a plan-view shape of the film-shaped tissue and opening downward, and a lower end thereof making contact with a bottom section of the container main body to thereby close the lower opening portion;

an interposed unit having elasticity and being sandwiched between the internal container and the lid member; and a storage fluid with which the internal container is filled to such an extent that no gas layer is formed within the internal container;

wherein the internal container has a liquid-permeable wall section which faces the bottom section of the container main body with a spacing therebetween and is configured so as to permit passage of liquid therethrough; and wherein the film-shaped tissue is present in a floating state in the storage fluid with which the internal container is filled.

2. The storage transport container for film-shaped tissue according to claim 1, wherein the internal container and the interposed unit make secure contact with each other to thereby establish a liquid-tight sealing between the internal container and the interposed unit.

3. The storage transport container for film-shaped tissue according to claim 2, wherein the internal container has a tube-shaped section opening upward and downward, and the liquid-permeable wall section is provided at an intermediate position in the height direction of the tube-shaped section and is configured in a mesh form.

4. The storage transport container for film-shaped tissue according to claim 3, wherein the interposed unit is disposed above the liquid-permeable wall section in a state of making contact with an inner circumferential surface of the tube-shaped section over the whole circumference in the circumferential direction.

5. The storage transport container for film-shaped tissue according to claim 2, wherein the liquid-permeable wall section is a plate-shaped body provided with at least one through-hole piercing therethrough in a vertical direction, and the at least one through-hole is closed by the interposed unit.

6. The storage transport container for film-shaped tissue according to claim 5, wherein the least one through-hole comprises a plurality of through-holes.

7. The storage transport container for film-shaped tissue according to claim 5, wherein the at least one through-hole comprises a single through-hole.

8. The storage transport container for film-shaped tissue according to claim 1, wherein the liquid-permeable wall section is provided with at least one through-hole piercing therethrough in a vertical direction, and a closing member closing the through-hole is disposed between the liquid-permeable wall section and the interposed unit.

9. The storage transport container for film-shaped tissue according to claim 8, wherein the closing member includes a closing plate portion and a hand grip portion.

10. The storage transport container for film-shaped tissue according to claim 1, wherein a liquid the same as or different from the storage fluid is present outside the internal container within the external container.

11. The storage transport container for film-shaped tissue according to claim 7, further comprising a stabilization member floating at a liquid surface of the liquid present outside the internal container within the external container.

12. The storage transport container for film-shaped tissue according to claim 1, wherein the bottom section includes a position restricting portion, the internal container being positioned within the position receiving portion of the bottom section.

13. The storage transport container for film-shaped tissue according to claim 1, wherein the coupling mechanism includes at least one clip.

14. The storage transport container for film-shaped tissue according to claim 1, wherein the coupling mechanism includes a screw engagement mechanism.

* * * * *